United States Patent [19]

Ikeda

[11] 4,248,246
[45] Feb. 3, 1981

[54] SAMPLING NEEDLE PROTECTOR

[75] Inventor: Tatsuhiko Ikeda, Musashino, Japan

[73] Assignee: Terumo Corporation, Tokyo, Japan

[21] Appl. No.: 54,905

[22] Filed: Jul. 5, 1979

[30] Foreign Application Priority Data

Jul. 28, 1978 [JP] Japan ............................ 53/92385

[51] Int. Cl.³ .............................................. A61B 5/14
[52] U.S. Cl. ................................ 128/765; 128/218 R
[58] Field of Search ........................... 128/763–766,
128/760, 218 R, 218 M, 218 N, 220, 221

[56] References Cited

U.S. PATENT DOCUMENTS

| 2,400,722 | 5/1946 | Swan | 128/215 X |
| 2,551,414 | 5/1951 | Burnside | 128/218 N |
| 2,896,622 | 7/1959 | Hüttermann | 128/218 M X |
| 3,162,195 | 12/1964 | Dick | 128/764 |
| 3,366,103 | 1/1968 | Keller | 128/218 R |
| 4,085,737 | 4/1978 | Bordow | 128/763 |
| 4,124,025 | 11/1978 | Alrazi | 128/218 R |

Primary Examiner—Kyle L. Howell
Attorney, Agent, or Firm—Frishauf, Holtz, Goodman & Woodward

[57] ABSTRACT

A protector for enclosing the needle body of a sampling needle after collection of blood or coeliac liquid comprises a cylindrical member having a hydrophilic inner wall and whose base end is opened, the inner wall of said opening being so shaped as to ensure engagement with the hub of the sampling needle; and a seal material filled in the cylindrical member for embedment of at least the end opening of the sampling needle therein.

6 Claims, 6 Drawing Figures

SAMPLING NEEDLE PROTECTOR

BACKGROUND OF THE INVENTION

This invention relates to a protector for a blood or coeliac liquid-sampling needle which, after collection of blood or coeliac liquid, seals the end opening of the sampling needle for protection.

After the collection of blood by a sampling needle for measurement of the quantity of a blood gas, the sampling needle has hitherto been thrust into a rubber cock or block to prevent the collected blood from leaking out or being brought into contact with air and also to protect the end portion of the sampling needle. However, such customary practice tends to cause the operator's hands or fingers to be wounded by the tip of the sampling needle which happens to pierce throughout the rubber material. Moreover, since the sampling needle is generally left bare, the operator is in danger of touching the collected blood of, for example, a patient which has leaked from the sampling needle, probably leading to the possiblity of being infected by the later described disease through said wounded parts. Therefore, the operator must use great caution in handling the sampling needle.

Further, where the sampling needle is simply thrust into a rubber cock or block, then difficulties arise that if undergoing vibrations or shocks during, for example, transit, the sampling needle comes off the rubber cock or block with relative ease, causing the blood to leak out or be contacted by the atmosphere. If, in case measurement is to be made of the quantity of a gas contained in the blood or coeliac liquid, a sample to be tested is brought into contact with the atmosphere or air is carried into the sample, then the results of said measurement will be prominently affected by such happenings, failing to provide accurate data on the quantity of blood gas. Therefore, the result of a single test has hitherto been regarded as unreliable. Further, each time a test is carried out, a sampling needle fitted to a sampler has to be taken off directly by hand. In this case, the removal of the sampling needle is accompanied with great difficulties, giving rise to the drawback that the operator's hands or clothing is often soiled due to the leakage of collected blood. Difficulties the same as described above also take place, where a coeliac liquid is sampled.

SUMMARY OF THE INVENTION

This invention has been accomplished in view of the above-mentioned circumstances, and is intended to provide a protector for a sampling needle used with a sampling device for collecting blood or coeliac liquid, which seals the end opening of the sampling needle after collection of the sample, protects the body of the sampling needle and also enables the sampling needle to be easily taken off the sampling device.

To attain the above-mentioned object, this invention provides a protector for a sampling needle used with a sampling device for collecting blood or coeliac liquid, which comprises a cylindrical member, at least one end of which is provided with an opening for the insertion of a sampling needle, the inner wall of said opening being hydrophilic and being so shaped as to ensure engagement with the hub of the sampling needle; and a seal material filled in the cylindrical member to allow for the embedment of at least the end opening of the sampling needle.

DETAILED DESCRIPTION OF THE PREFERRED EMBODIMENTS

There will now be described by reference to the accompanying drawings a sampling needle protector embodying this invention. Throughout the drawings, the same parts are denoted by the same numerals.

Figure 1:
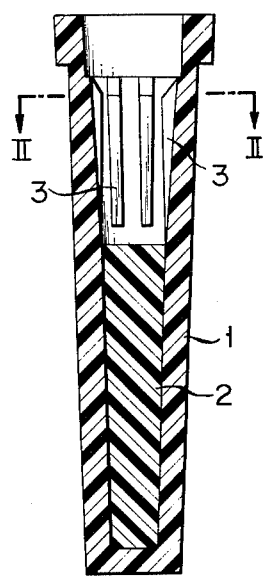
FIG. 1 is a sectional view of a sampling needle protector according to one embodiment of this invention.
Figure 2:
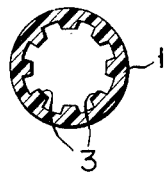
FIG. 2 is a sectional view on line II-II of FIG. 1.
Figure 3:
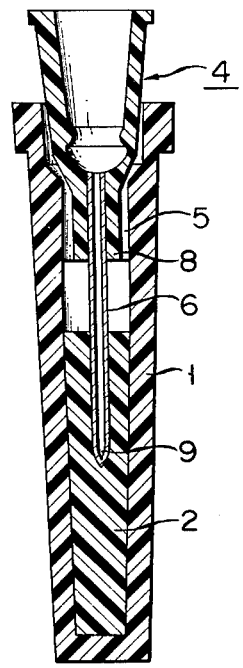
FIG. 3 is a sectional view of a sampling needle inserted into the protector of FIG. 1.

There will now be described by reference to FIG. 1 a sampling needle protector according to one embodiment of this invention, which is used with a sampling device for collecting blood or coeliac liquid. The protector essentially comprises a cylindrical member 1 open at one end and a seal material 2 filled in said cylindrical member 1. The cylindrical member 1 is molded from a synthetic resin, for example, polypropylene. A plurality of axially extending ribs 3 are projectively formed in parallel at a substantially equal interval on that portion of the inner wall of the cylindrical member 1 which lies near the opening. When a sampling needle 4 is removed from a blood or coeliac liquid-sampling device (not shown), the ribs 3 abut against the side walls of a plurality of ribs 5 formed on the surface of the hub of the sampling needle 4, thereby enabling the sampling needle 4 to be easily removed from the sampling device while said needle 4 is rotated. The seal material is preferred to be of the type that a smaller load than 2 kg has only to be applied to pierce in a normal direction into the seal material by a sampling needle of 20 gauge (having an outer diameter of 0.90 mm) to a depth of 10 mm; and where the plunger of a syringe fitted with the sampling needle pushes a sample liquid received in the syringe even with a load of 1 kg, the sample liquid does not leak out of the sampling needle. In other words, the seal material should mainly consist of fine powders of inorganic or organic material, for example, clays made properly viscous by applying nonvolatile oil, putty material, for example, a mixture of polyvinyl chloride and dioctyl phthalate, paraffin having a melting point of 48° to 54° C., or polyurethane having a Shore A hardness of 25° to 35°.

Figure 4:
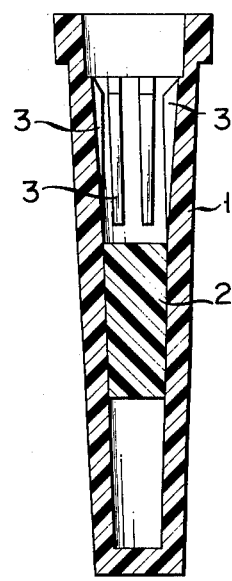
FIGS. 4 and 5 are sectional views of sampling needle protectors according to other embodiments of the invention.

The seal material 2 should preferably be filled in the cylinder 1 in such amount as causes one third of the length of the body 6 of the sampling needle 4 to be embedded in the seal material 2 when the sampling needle 4 is fully inserted into the cylinder 1. Depending on the kind, however, the seal material 2 may be filled in the cylinder 1 in a larger or smaller amount than described above. Further, where the seal material 2 is formed of the above-mentioned clay or putty, part of which is easily carried into the void cavity of the sampling needle 4 when it is thrust into the seal material 2, then said seal material 2 may be filled only in the intermediate section of the cylinder 1, as shown in FIG. 4.

A seal material 2 such as clay or putty which has a high melting point can be simply forced into the cylinder 1 at its opening. Where the seal material 2 is of the low melting point type such as paraffin, then, it is advised to thermally melt the seal material and pour it into the cylinder 1 in small divided parts by an applicator. Where polyurethane is used as the seal material 2, it is advised to prepare said polyurethane by mixing a prepolymer whose end radical includes isocyanate with polyol for reaction and pour the resultant polyurethane into the cylinder 1 in small divided parts by an applicator. A polyurethane seal material having a lower Shore A hardness than 25° has a low sealing property with respect to the sampling needle 4. Conversely, a polyurethane seal material having a higher Shore A hardness than 35° is pierced by the sampling needle 4 with greater difficulty, and proves unadapted for practical application. Where the cylinder 1 is made of an olefinic material, for example, polypropylene, then the polyurethane seal material 2 can not be closely fitted to said cylinder 1, possibly giving rise to a gap between the cylinder 1 and seal material 2. Therefore, it is preferred to render the inner wall of the cylinder 1 hydrophilic by applying, for example, plasma discharge.

Figure 5:
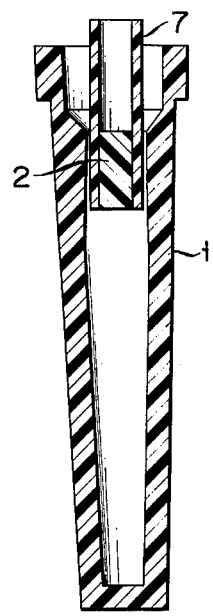

Another preferred process of filling the seal material 2 in the cylinder 1 is to previously fill the seal material 2 in a tube 7 prepared from soft plastic material such as polyvinyl chloride resin and insert said tube 7 into the protector 1 as shown in FIG. 5. This arrangement enables the sampling needle 4 to be reliably sealed by the seal material 2 regardless of the length of the needle body and offers the advantage of reducing the amount of the seal material 2 to be used. The tube 7 should have such an outer diameter as can hold the tube 7 near the opening of the protector 1 and yet enable the tube 7 to slide toward the bottom of the protector 1 and also a smaller inner diameter than that of the end 8 of the base portion of the sampling needle 4. The tube 7 is preferred to have a length about one third that of the protector 1.

Figure 6:
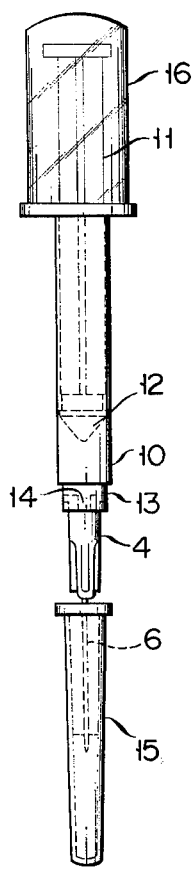
FIG. 6 is a side view showing the manner in which the protector of the invention is practically applied.

A sampling device comprises, as shown in FIG. 6, a plunger 11 which is made from synthetic resin and whose end is fitted with a freely movable gasket 12 and an outer cylinder 10 closely enclosing said plunger 11. A truncated round conical fitting member 14 is projectively provided at the center of the end portion of the cylinder 10. An auxiliary fitting member 13 whose inner wall is threaded is mounted on the outer peripheral wall of the fitting member 14.

There will now be described by reference to FIG. 6 the application of a sampling needle protector constructed as described above. First, the sampling needle 4 is fitted to the sampling device to collect blood from the artery of a patient. The operator holds the sampling device fitted with the sampling needle 4 by one hand and the protector 15 by the other hand. The sampling needle 4 is inserted into the protector 15. At this time, the end portion 4a of the sampling needle 4 pierces the seal material 2 to cause the end opening 9 of the sampling needle 4 to be tightly closely by the seal material 2. The sampling device thus arranged is brought to a test room. If, at this time, the plunger 11 happens to be forcefully pushed, the protector 15 is likely to be taken off. Therefore, it is preferred to fit a cap 16 to the sampling device in order to prevent the plunger 11 from being pushed. Before the quantity of a blood gas is measured, the sampling needle 4 is removed from the sampling device in a state still received in the protector 15. At this time, the operator holds the sampling device by one hand, and rotates the protector 15 by the other hand. At this time, the ribs 3 formed on the inner wall of the protector 15 and the ribs 5 formed or the outer peripheral surface of the hub of the sampling needle 4 engage each other, enabling the sampling needle 4 to be easily taken off the fitting member of the sampling device in a state still received in the protector 15. The sampling needle thus protected is brought to the test room, where the quantity of blood gas can be measured easily and reliably with the least possibility of the blood being contaminated by the atmospheric air or any other foreign matter and also with the operator saved from injuries resulting from the perchance prick of the tip of the sampling needle 4 or with his hands and clothing prevented from being soiled with leaking blood.

There will now be described by reference to FIG. 5 the case where the seal material 2 is previously filled in the tube 7, and this tube 7 is inserted into the protector or cylinder 1. After the artery blood is collected, the sampling needle 4 is inserted into the tube 7 in a state still fitted to the sampling device. At that time, the sampling needle 4 pierces the seal material 2, causing the end opening 9 thereof to be closed with the seal material 2. Where the sampling needle 4 is further inserted into the protector 1, then the tube 7 is pushed downward through the protector 1 by the end 8 of the base portion of the sampling needle 4. Finally, the ribs 5 formed on the hub of the sampling needle 4 are engaged with the ribs 3 formed on the inner wall of the protector 1.

According to this invention, the seal material 2 pierced by the sampling needle 4 is filled in the protector 1. When the sampling needle 4 is inserted into the seal material 2 filled in the cylinder 1, after blood or coeliac liquid is collected by the sampling device, then the end opening of the sampling needle 4 is automatically closed with the seal material 2 to prevent the collected blood or coeliac liquid from being brought into contact with the atmosphere. Even where the sampling device happens to be subjected to vibrations or shocks, the sampling needle 4 is prevented from coming off by being inserted into the seal material 2 filled in the protector 1. Therefore, collected blood or coeliac liquid is not contacted by the atmospheric air during either storage or transit. Therefore, a single test can provide accurate data on the quantity of a blood gas. Since the device of the sampling needle is enclosed in a protector, the operator has little chance to touch the collected blood of a patient. If, therefore, the operator's hands or fingers happen to be injured beforehand, the collected blood will not enter the operator's blood vessel through the wounded part. This protective arrangement helps to prevent a hospital operator from being infected by a disease such as serum hepatitis.

This invention offers the advantage of easily and safely removing the sampling needle 4 from the sampling device when the quantity of a blood gas is measured. At present, measurement of the quantity of a blood gas is used in various applications including the detection of the affected condition of a patient suffering from a serious disease such as respiration failure or heart failure. A large number of blood samples are now being collected. Therefore, a sampling device provided with a sampling needle protector embodying this invention proves very useful in that the process of pouring collected sample blood or coeliac liquid in a testing apparatus in small divided parts can be carried out quickly and safely.

With the foregoing embodiment, the cylindrical protector of a sampling needle was closed at one end. However, the protector need not be restricted to this type, but may be open at said end. Further, a plurality of ribs were formed on the inner wall of the sampling needle protector for engagement with the ribs formed on the outer peripheral wall of the sampling needle hub. However, the engagement means need not be restricted to the ribs, but may be formed of any other suitable type. For instance, the opening of the cylindrical protector may be made polygonal for engagement with the sampling needle hub.

What is claimed is:

1. A protector for a sampling needle of a sampling device for collecting blood or coeliac liquid, the sampling needle having a hub and an elongated needle extending therefrom, the needle having an end opening; the sampling device including a syringe having a plunger, and means for engagement with said sampling needle; the protector comprising:

a cylindrical member having a hydrophilic inner wall, at least one end of said cylindrical member having an opening for insertion of a sampling needle therein, the inner wall of said opening having engagement means for engaging the hub of a sampling needle inserted into the opening; and a seal material filled in the interior of said cylindrical member and into which said sampling needle is insertable for embedding at least the end opening of the sampling needle therein, the seal material being formed of the substance which is pierceable by a 20-gauge sampling needle to a depth of 10 mm with a smaller load than 2 Kg, and which prevents a sample liquid received in a syringe from leaking out of the tip of the sampling needle even when the plunger of the syringe fitted with the sampling needle pushes the sample liquid with a load of 1 Kg.

2. The sampling needle protector according to claim 1, wherein the seal material is mainly formed of fine powders of inorganic or organic material.

3. The sampling needle protector according to claim 1, wherein the seal material is formed of paraffin having a melting point of 48° to 54° C.

4. The sampling needle protector according to claim 1, wherein the seal material comprises polyurethane having Shore A hardness of 25° to 35°.

5. The sampling needle protector according to claim 1, wherein said engagement means comprises a plurality of ribs formed on and projecting from the inner wall of said end opening of said protector.

6. The sampling needle protector according to any one of claims 1, 2, 3, 4 or 5, comprising a tube in which the seal material is filled, said tube being formed of soft plastic material and being received in said cylindrical member.

* * * * *